United States Patent [19]

Chari

[11] Patent Number: 5,620,632
[45] Date of Patent: Apr. 15, 1997

[54] DISPERSIONS OF EPOXY SCAVENGERS EXHIBITING IMPROVED RAW STOCK KEEPING

[75] Inventor: Krishnan Chari, Fairport, N.Y.

[73] Assignee: Eastman Kodak Company, Rochester, N.Y.

[21] Appl. No.: 427,763

[22] Filed: Apr. 25, 1995

[51] Int. Cl.$^6$ ............................ B01J 13/00; C08K 5/524; C09K 15/26
[52] U.S. Cl. .................... 252/311; 241/16; 252/312; 252/314; 252/402; 523/451; 524/145; 524/811
[58] Field of Search ...................... 252/311, 312, 252/314, 402; 241/16; 524/145, 710, 811; 523/451; 549/512

[56] References Cited

U.S. PATENT DOCUMENTS

| | | | |
|---|---|---|---|
| 3,936,303 | 2/1976 | Shiba et al. | 430/546 |
| 4,009,136 | 2/1977 | Lewandowski et al. | 524/145 X |
| 4,239,851 | 12/1980 | Aoki et al. | 430/377 |
| 4,253,999 | 3/1981 | Okishi | 252/312 X |
| 4,387,011 | 6/1983 | Makuuchi et al. | 525/530 X |
| 4,540,657 | 9/1985 | Krishnamurthy | 430/546 |
| 4,611,026 | 9/1986 | Olson et al. | 524/811 X |
| 4,621,112 | 11/1986 | Backhouse et al. | 524/145 |
| 4,745,052 | 5/1988 | Renner | 430/555 |
| 4,900,655 | 2/1990 | Nakazyo et al. | 430/546 |
| 5,001,045 | 3/1991 | Furutachi et al. | 430/545 |
| 5,037,730 | 8/1991 | Aoki et al. | 430/551 |
| 5,047,315 | 9/1991 | Morigaki et al. | 430/544 |
| 5,183,731 | 2/1993 | Takahashi et al. | 430/551 |
| 5,200,307 | 4/1993 | Takahashi | 430/507 |
| 5,284,907 | 2/1994 | Schulz et al. | 524/710 |
| 5,378,740 | 1/1995 | Ng | 524/145 X |
| 5,441,549 | 8/1995 | Helmin | 51/298 |
| 5,508,147 | 4/1996 | Chari et al. | 430/372 |

FOREIGN PATENT DOCUMENTS

| | | |
|---|---|---|
| 435179 | 7/1991 | European Pat. Off. . |
| 472153 | 2/1992 | European Pat. Off. . |
| 471347 | 2/1992 | European Pat. Off. . |
| 476604 | 3/1992 | European Pat. Off. . |
| 2432041 | 1/1975 | Germany . |
| 62-75448 | 4/1987 | Japan . |
| 62-131259 | 6/1987 | Japan . |
| 62-166331 | 7/1987 | Japan . |
| 62-201441 | 9/1987 | Japan . |

OTHER PUBLICATIONS

Derwent Abstract for Japanese Application No. 62/80,641 (1987).
Derwent Abstract for Japanese Application No. 62/129,853 (1987).
Derwent Abstract for Japanese Application No. 63/250,652 (1988).

Primary Examiner—Richard D. Lovering
Attorney, Agent, or Firm—Andrew J. Anderson

[57] ABSTRACT

A process for preparing a solid particle dispersion of an epoxy compound of the formula SI,

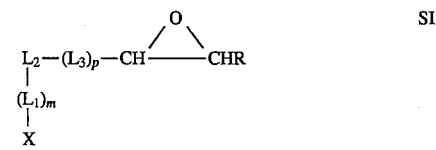

wherein R is H, an alkyl group, or an aryl group; $L_1$ is an alkylene group or an arylene group; $L_2$ is —O—, —CO—, —S—, —SO$_2$—, —PO$_2$—, —CO$_2$—, —NHCO— or —NHSO$_2$—, wherein $L_2$ may be orientated in either direction; $L_3$ is an alkylene group; m is 0 or 1; p is 0 or 1; and X is

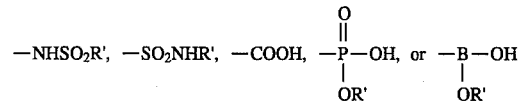

wherein R' is H or an alkyl or aryl group, with the proviso that where $L_2$ comprises an ionizable group, X may also be an alkyl group or an aryl group is disclosed. The process comprising the steps of: (a) forming a coarse aqueous slurry of solid particles of said compound; and (b) milling said slurry in the presence of a hydrophobic, photographically inert, liquid second component which has a logP$_{(calc)}$ greater than about 6.0 for time sufficient to provide particles of the desired average particle size. Solid particle dispersions of the invention exhibit improved raw stock keeping under conditions of elevated temperatures when incorporated in a photographic element.

14 Claims, No Drawings

DISPERSIONS OF EPOXY SCAVENGERS EXHIBITING IMPROVED RAW STOCK KEEPING

FIELD OF THE INVENTION

This invention relates to photographic elements. More particularly, this invention relates to silver halide color photographic elements comprising residual magenta coupler scavenger epoxy compounds having improved resistance to thermal and photochemical yellowing and improved raw stock keeping, and to methods of preparing such photographic elements and dispersions of such epoxy compounds.

BACKGROUND OF THE INVENTION

It is well known that thermal and photochemical yellowing are major concerns in magenta image stability of color prints. Over the years improvement in magenta image stability has been achieved by introducing more efficient image stabilizers. However, there still exists a need to further improve the resistance to yellowing in color paper.

It has been known for some time that compounds having the generic structure S are able to undergo reaction with residual magenta coupler and thereby effectively prevent both thermal and photochemical yellowing since the products of the reaction are not yellow and are not prone to yellowing. However, a major problem in the utilization of these compounds is the loss of coupler during storage of the photographic element prior to exposure and processing resulting in a reduction in color density in the print. See for example, U.S. Pat. No. 4,540,657 to Krishnamurthy and Japanese Patent Publication No. 62-31259 to Fuji Photo Film Co., Ltd. The generic structure of Compound S is represented below:

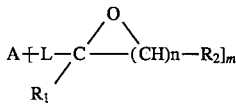

wherein: A is a polyvalent atom, an acidic oxide group, a carboxylic group, a heterocyclic moiety, a carbocyclic group, or an alkane or substituted alkane group; each L is at least one divalent linking group; $R_1$ and $R_2$ are H, alkyl, cycloalkyl, aryl, heterocyclic, ester; n is a positive integer with a range of 1–6; m is a positive integer of at least one; with the proviso that at least one of A, L, R or $R_2$ contains at least one ester or amide group derived from an acidic oxide of carbon, phosphorous, sulfur, boron or silicon.

In copending, commonly assigned application U.S. Ser. No. 08/000,431, filed Jan. 4, 1993, now U.S. Pat. No. 5,508,147, the disclosure of which is hereby incorporated by reference, we showed that the compound S-1 (having the structural formula set forth below) could be incorporated in a silver halide color photographic element containing a ballasted magenta coupler such that there is negligible loss of coupler prior to processing. This was achieved by coating the epoxy compound in separate layers that were adjacent to the imaging layer containing the magenta coupler and the green sensitized emulsion. Furthermore, it has also been demonstrated that mixing of S-1 with residual magenta coupler after processing may be achieved by using a pH dependent solubilizing agent, e.g., a fatty acid, such as myristic acid, in the coating and processing the coating using developer which preferably contains benzyl alcohol. However, the use of benzyl alcohol in the developer raises environmental concerns.

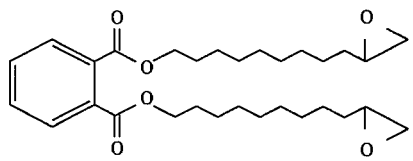

In an effort to eliminate the use of compounds such as benzyl alcohol to achieve post process mixing of the epoxy scavenger with the residual magenta coupler, copending, commonly assigned U.S. Ser. No. 08/255,512, filed Jun. 8, 1994, and now U.S. Pat. No. 5,543,276, the disclosure of which is hereby incorporated by reference, discloses novel terminal epoxy compounds containing a pH-dependent solubilizing moiety in the molecule. Dispersions of these compounds are coated in layers adjacent to the magenta imaging layer, and the compounds diffuse into the magenta layer upon processing where they react with residual magenta coupler yielding products that are not yellow or prone to yellowing. The approach is effective in reducing thermal and photochemical yellowing in processed prints without the use of benzyl alcohol.

The exemplified compounds disclosed in U.S. Ser. No. 08/255,512 now U.S. Pat. No. 5,543,276, are incorporated into photographic elements in the form of solid particle dispersions. It has been previously proposed in the photographic art to use solid particle dispersions as a means for incorporation of a variety of photographically useful compounds, for example, solid particle filter dye dispersions, as disclosed in, e.g., U.S. Pat. Nos. 4,294,916, 4,294,917, and U.S. Pat. No. 4,940,654. Techniques for making solid particle dispersions are very different from the techniques used to make conventional oil-in-water photographic dispersions. Typically, solid particle dispersions are made by mixing the solid of interest with an aqueous solution that may contain one or more grinding aids or stabilizers. Particle size reduction is accomplished by subjecting the solid crystals in the slurry to repeated collisions with hard, inorganic milling media, such as sand, spheres of silica, stainless steels silicon carbide, glass, zirconium, zirconium oxide, yttria-stabilized zirconium oxide, alumina, titanium etc., all of which fracture the crystals. The bead sizes typically range from 0.25 to 3.0 millimeters (mm) in diameter. Ball mills, media mills, attritor mills, jet mills, vibratory mills, etc. are frequently used to accomplish particle size reduction.

Problems have been identified, however, when photographic materials containing the epoxy compounds disclosed in U.S. Ser. No. 08/255,512 now U.S. Pat. No. 5,543,276, are stored at elevated temperatures (e.g., above about 45° C.) prior to exposure and processing. Typically, it is found that there is significant loss in color density in the high exposure (or highlight) regions of the print if these materials are stored at elevated temperatures for long periods of time prior to exposure and processing. The latter is believed to result from unwanted migration of the epoxy compound from the adjacent nonimaging layer to the magenta imaging layer prior to processing. A method is therefore desired to improve the raw stock keeping properties of these materials at elevated temperatures.

SUMMARY OF THE INVENTION

It is the object of this invention to provide a silver halide based color photographic element containing residual magenta coupler scavenger epoxy compounds having significantly improved raw stock keeping. It is a further object of this invention to provide a color photographic paper having such improved properties.

These and other objectives of the invention are realized by incorporating the epoxy compounds in the form of solid particle dispersions, wherein the solid particle dispersions are prepared by milling the compound in the presence of a small amount of a second component.

One embodiment of the invention comprises a process for preparing a solid particle dispersion of an epoxy compound of the formula SI,

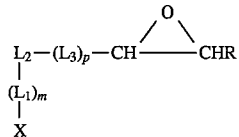

wherein R is H, an alkyl group, or an aryl group; $L_1$ is an alkylene group or arylene group; $L_2$ is —O—, —CO—, —S—, —SO$_2$—, —PO$_2$—, —C$_2$—, —NHCO— or —NHSO$_2$—, wherein $L_2$ may be orientated in either direction; $L_3$ is an alkylene group; m is 0 or 1; p is 0 or 1; and X is

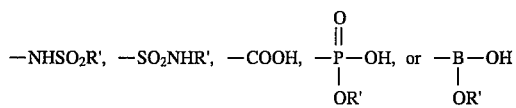

wherein R' is H or an alkyl or aryl group, with the proviso that where $L_2$ comprises an ionizable group, X may also be an alkyl group or an aryl group;

said process comprising the steps of:
(a) forming a coarse aqueous slurry of solid particles of said compound; and
(b) milling said slurry in the presence of a hydrophobic, photographically inert, liquid second component which has a logP$_{(calc)}$ greater than about 6.0 for time sufficient to provide particles of the desired average particle size.

Further embodiments of the invention include dispersions of compounds of formula SI made from such a process, and photographic elements comprising a support bearing thereon: (a) a photosensitive first layer comprising (i) a silver halide emulsion, and (ii) a magenta coupler dispersion; and (b) a second layer comprising a solid particle dispersion of an epoxy compound of formula SI produced by such process.

DETAILED DESCRIPTION OF THE INVENTION

The substituent groups in Formula SI can be unsubstituted or further substituted with photographically acceptable substituents. Typical examples of photographic substituents include alkyl, aryl, anilino, carbonamido, sulfonamido, alkylthio, arylthio, alkenyl, cycloalkyl, and further to these exemplified are halogen, cycloalkenyl, alkinyl, heterocyclyl, sulfonyl, sulfinyl, phosphonyl, acyl, carbamoyl, sulfamoyl, cyano, alkoxy, aryloxy, heterocyclyloxy, siloxy, acyloxy, carbamoyloxy, amino, alkylamino, imido, ureido, sulfamoylamino, alkoxycarbonylamino, aryloxycarbonylamino, alkoxycarbonyl, aryloxycarbonyl, heterocyclylthio, spiro compound residues and bridged hydrocarbon compound residues. Usually the substituent will have less than 30 carbon atoms and typically less than 20 carbon atoms. It is understood throughout this specification that any reference to a substituent by the identification of a group containing a substitutable hydrogen (e.g. alkyl, amine, aryl, alkoxy, heterocyclic, etc.), unless otherwise specifically stated, shall encompass not only the substituent's unsubstituted form, but also its form substituted with any other photographically useful substituents.

Preferred substituents on the alkyl and aryl groups of Formula SI are hydrocarbyl groups, one or more hetero atoms, such as chlorine and the like or one or more hetero groups containing for example, N, P, S, etc. R in Formula SI is preferably H or alkyl, such as methyl, ethyl, etc.

Preferred compounds of Formula SI for use in the invention include those wherein m and p are each 1, $L_1$ is phenylene, $L_2$ is —O—, —CO—, —SO$_2$—, —PO$_2$—, or —CO$_2$—, $L_3$ is a linear or branched alkylene group, X is —NHSO$_2$R', —SO$_2$NHR', —COOH,

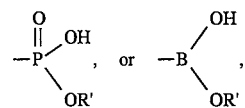

and R' is an alkyl or aryl group. Most preferred are compounds of the formula:

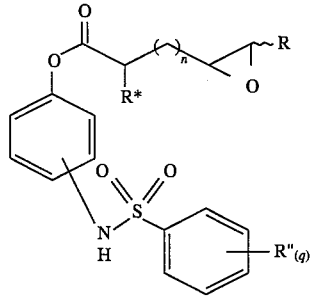

wherein: R* is H or an alkyl or aryl group; n is from 1 to about 20; q is 1, 2, or 3; and each R" is H, an alkoxide group, a phosphate group, a sulfate group, a sulfonamide group, a sulfone group, a halogen atom, or an alkyl group.

A general scheme for the synthesis of preferred compounds of Formula SI is as follows:

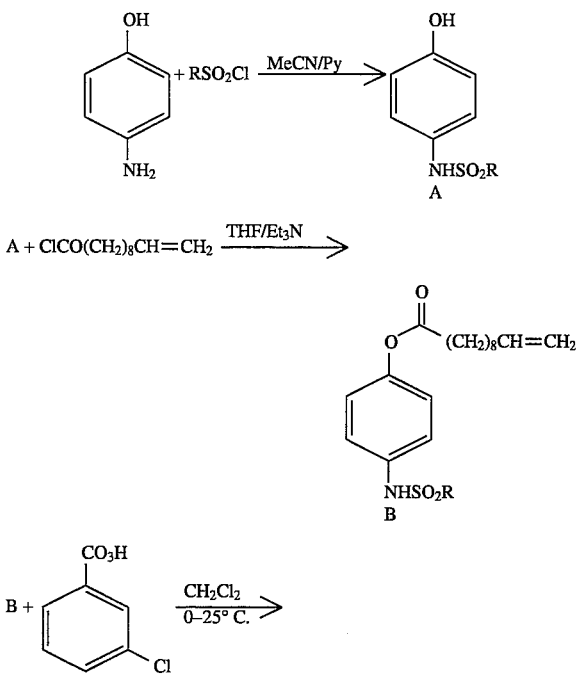

R = substituted alkyl or aryl

Illustrative epoxy compounds of this invention are:

-continued
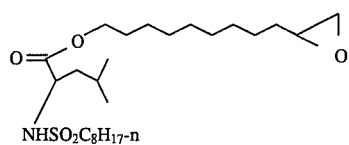
SI-12
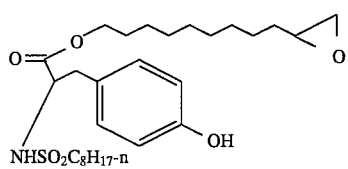
SI-13
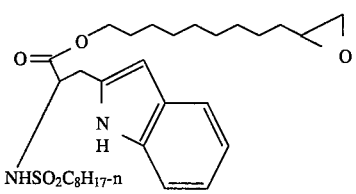
SI-14
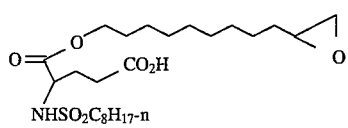
SI-15
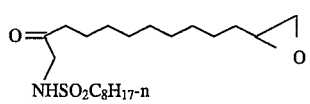
SI-16
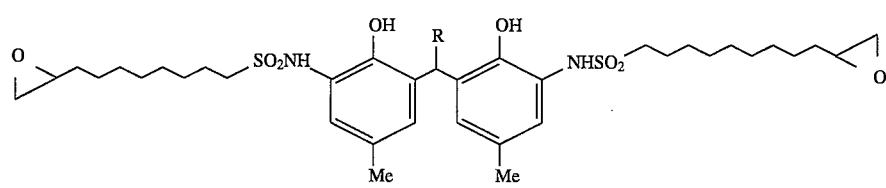
SI-17
R = H, Me
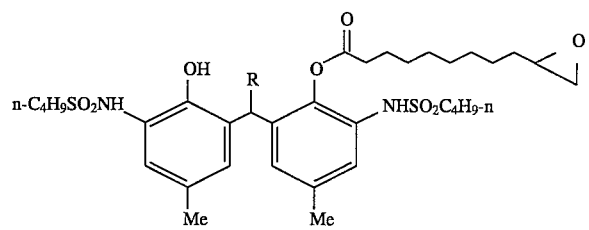
SI-18
R = H, Me
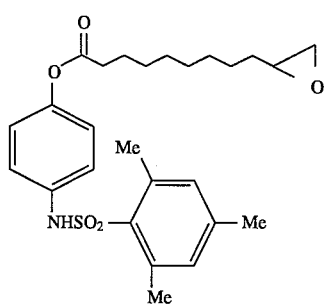
SI-19
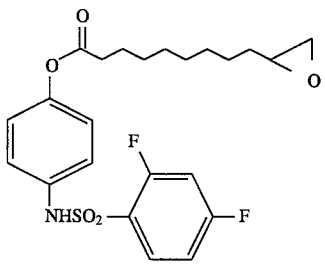
SI-20
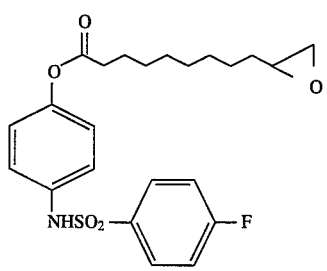
SI-21

Specific compounds of a preferred structure of SI are:

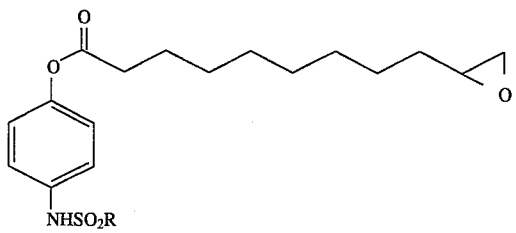

wherein:

| R | Compound Number |
|---|---|
| n-$C_4H_9$ | SI-2 |
|  | SI-19 |

| R | Compound Number |
|---|---|
| 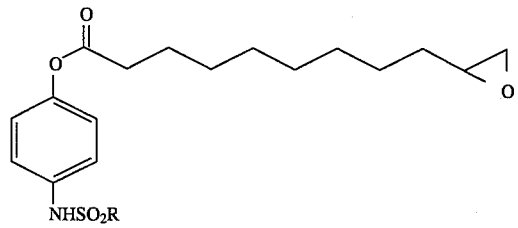 | SI-20 |
| | SI-21 |

Physical properties of selected SI compounds having the formula set forth below with R as defined in the following table are:

Melting Points and Log P values for Selected Examples

| SI-n | R | mp (°C.) | LogP* |
|---|---|---|---|
| (SI-1) | $-CH_3$ | 100–101 | 2.7 |
| (SI-2) | n-$C_4H_9$ | 69–70 | 4.3 |
| (SI-3) | n-$C_{10}H_{21}$ | 88–89 | 7.5 |
| (SI-19) | 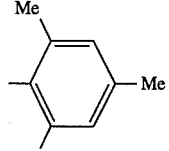 | 77–78 | 5.9 |
| (SI-20) | 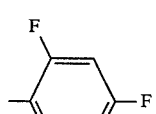 | 77(s) | 4.5 |
| (SI-21) |  | 56–69 | 4.6 |
| (S-1) (Comparative) | 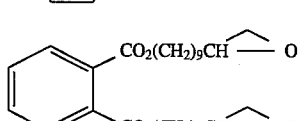 | oil | 7.0 |

*Log P values are calculated values of the octanol/water partition coefficient of the compound and were calculated using Med Chem v. 3.54, a software package available from the Medicinal Chemistry Project, Pomona College, Claremont, California.

We have found that certain components can effectively improve raw stock keeping of photographic elements comprising solid particle dispersions of residual magenta coupler scavenger epoxy. The components are hydrophobic, photographically inert compounds that have a $logP_{(calc)}$ of at least about 6, more preferably at least about 8 and most preferably at least about 9, where $logP_{(calc)}$ is the logarithm of the value of the octanol/water partition coefficient (P) of the compound calculated using MedChem, version 3.54, a software package available from the Medicinal Chemistry Project, Pomona College, Claremont, Calif. Such compounds preferably have a solubility in water of less than 1.0 μg/mL. $\text{LogP}_{(calc)}$ is a parameter which is highly correlated with measured water solubility for compounds spanning a wide range of hydrophobicity. Compounds having a high $\text{logP}_{(calc)}$ may be so highly hydrophobic that it is difficult to measure their water solubility using standard techniques. $\text{LogP}_{(calc)}$ is a useful means to characterize their hydrophobicity.

In accordance with this invention, raw stock keeping of photographic elements incorporating milled solid particles of epoxy compounds of formula SI can be improved by the use of hydrophobic, photographically inert liquid substances during the milling process. The hydrophobic, photographically inert compounds used in this invention are liquids during milling and have a $\text{logP}_{(calc)}$ greater than about 6. Preferred hydrophobic, photographically inert compounds are those selected from the following classes of compounds:

I. alkanes, alkenes or alkyl halides having a $\text{logP}_{(calc)}$ greater than about 6, II. compounds which have an elemental composition consisting of carbon, hydrogen, and oxygen and a $\text{logP}_{(calc)}$ greater than about 6, III. Esters and amides of sulfur or phosphorous acids having a $\text{logP}_{(calc)}$ greater than about 6, IV. Amides and amines having a $\text{logP}_{(calc)}$ greater than about 6.

Representative compounds are given below, along with their $\text{logP}_{(calc)}$ value. Each $\text{Log P}_{(calc)}$ was calculated using the above-mentioned MedChem software package (version 3.54). This software package is well known and accepted in the chemical and pharmaceutical industries.

Compounds of class I include: straight or branched chain alkanes and alkenes such as, for example, hexadecane and octadecene, and haloalkanes such as hexadecyl bromide and octadecyl chloride.

Compounds of class II include any liquid with a calculated $\text{logP}_{(calc)}$ greater than about 6 and with an elemental composition consisting of carbon, hydrogen, and oxygen. Such compounds include, for example, diesters such as bis(2-ethylhexyl) azelate, substituted aromatic compounds such as phthalates, isophthalates, and terephthalates, including for example, dinonyl phthalate, didecylphthalate, and didodecylphthalate.

Compounds of class III include esters and amides of sulfur or phosphorous acids including, for example, sulfates, sulfonates, sulfonamides, phosphates, phosphonates, phosphites, and phosphine oxides. Particular examples include triesters of phosphoric acid, such as tri(2-ethylhexyl) phosphate, and trisubstituted phosphine oxides, such as trioctylphosphine oxide.

Compounds of class IV include, for example, trioctyl amine.

Representative compounds and their respective $\text{logP}_{(calc)}$ values are given below:

1. hexadecane (9.16)
2. bis (2-ethylhexyl)azelate (9.20)
3. tri (2-ethylhexyl) phosphate (9.49)
4. trioctylphosphine oxide (9.74)
5. didecyl phthalate (11.04)
6. trioctyl amine (10.76)
7. tritolyl phosphate (6.58)
8. 2,4-di-tert-pentylphenol (6.49)
9. 1,4-cyclohexanedimethanol bis(2-ethylhexanoate) (8.14)
10. oleyl alcohol (7.69)
11. p-dodecylphenol (7.94)
12. trihexyl phosphate (6.70)
13. isopropyl palmitate (8.39)
14. dihexyl hexylphosphonate (6.32)
15. dodecylbenzene (8.61)

Some of the hydrophobic, photographically inert components useful in the practice of this invention have been disclosed to be useful in photographic dispersions as permanent solvents for couplers or other photographically useful compounds. Such use is directed towards conventional oil-in-water dispersions, rather than the solid particle dispersions of the invention.

The dispersions of this invention are formed by milling an epoxy compound of formula SI in the presence of a photographically inert liquid compound. Where the melting point of the photographically inert compound is below room temperature (which is preferred), milling may be done at room temperature. Alternatively, milling may be performed at elevated temperatures above the melting point of photographically inert compounds which are not liquids at room temperature. While the hydrophobic, photographically inert substance in accordance with the invention is used at a sufficient level to have an effect on the raw stock keeping (generally above 0.01 wt% based upon the weight of the milled epoxy compound, and preferably above 1 wt%), the preferred amount of hydrophobic, photographically inert substance for use in this invention is a level less than the total amount of epoxy compound of formula SI. The more preferred level of hydrophobic, photographically inert substance is less than one half the weight of the epoxy compound of formula SI. The most preferred level of hydrophobic, photographically inert compound is less than or about one fourth the weight of the epoxy compound of formula SI.

It has been found that many conventional compounds which are used as image light stabilizers for magenta image dyes can severely inhibit the post-process reaction between residual magenta coupler and the epoxy compounds of the invention and thereby suppress the beneficial effects of the epoxy compounds on yellowing. In a preferred embodiment of the invention, the epoxy compounds are used in combination with image stabilizers for the magenta image dye such that there is little or no inhibition of the post-process reaction between the epoxy compound and residual magenta coupler. Such embodiment comprises using an image stabilizer of the following formula STG-A in the photosensitive layer of the elements of the invention comprising a magenta coupler dispersion.

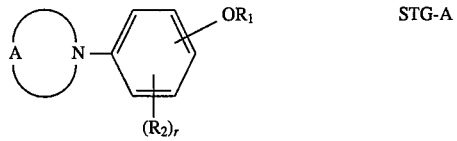

STG-A wherein $R_1$ represents an alkyl group, a cycloalkyl group, an alkenyl phenyl group, an aryl group, a heterocyclic group, an acyl group, a bridged hydrocarbon group, an alkyl sulfonyl group or an aryl sulfonyl group; $R_2$ represents a group capable of being substituted on the benzene ring; r represents an integer between 0 and 4; and A represents a group of non metal atoms necessary for the formation of a 5 to 8 membered ring together with the nitrogen atom. Use of such image stabilizers with residual magenta coupler scavenger epoxy compounds is the subject matter of concurrently filed, commonly assigned, copending application U.S. Ser. No. 08/429,269 (Kodak Docket No. 71731AJA), the disclosure of which is incorporated by reference.

The magenta dye forming coupler is preferably a pyrazolone, pyrazolotriazole, pyrazolobenzimidazole with or without a suitable leaving group. The magenta coupler can be monomeric, dimeric, trimeric, oligomeric or polymeric coupler wherein the coupler moiety can be attached to the polymeric backbone via a substituent on the coupler moiety or a substituent on a coupling off group. Illustrative magenta couplers are disclosed in, for example, U.S. Pat. Nos. 1,969,479; 2,311,082; 2,343,703; 2,369,489; 2,575,182; 2,600,788; 2,706,685; 2,908,573; 3,061,432; 3,062,653; 3,152,896; 3,153,816; 3,214,437; 3,253,924; 3,311,476; 3,419,391; 3,519,429; 3,725,067; 3,770,447; 3,907,571; 3,928,044; 3,935,015; 4,120,723; 4,123,281; 4,199,361; 4,336,325; 4,351,897; 4,385,111; 4,401,752; 4,407,936; 4,413,054; 4,283,472; 4,338,393; 4,420,556; 4,443,536; 4,500,630; 4,522,915; 4,540,654; 4,576,912; 4,581,326; 4,621,046; 4,728,598; 4,774,172; and 4,853,319 European Patent Applications Nos. 284,239; 284,240; 240,852; 170,164; and 177,765; Japanese Patent Publication Nos. 60/170854, 60/194451 and 60/194452 and Great Britain Patents Nos. 1,047,612, 1,357,372 and 1,530,272, and "Farbkuppler-eine Literaturübersicht", published in Agfa Mitteilungen, Band III, pp 126–156 (1961); the disclosures of which are incorporated herein by reference.

Magenta dye-forming couplers comprise pyrazolone compounds of the general formula:

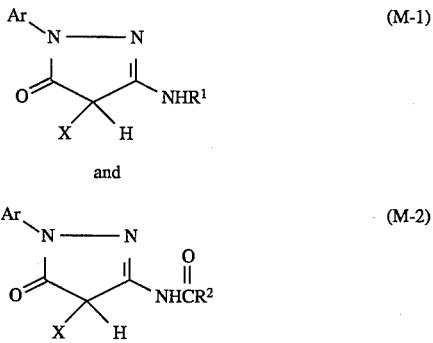

pyrazolotriazole compounds of the general formula:

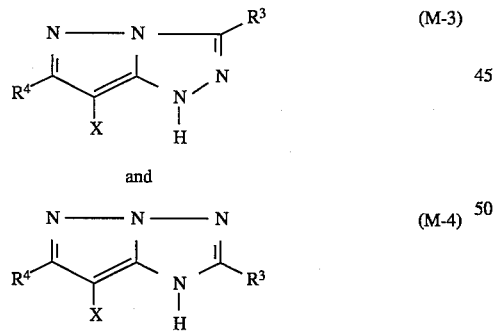

and pyrazolobenzimidazoles of the formula:

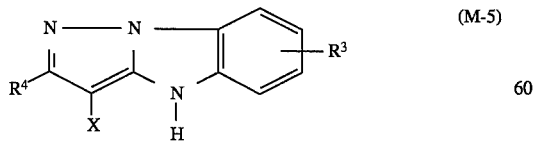

wherein

Ar is an unsubstituted aryl group or an aryl group (including pyridyl) substituted with one or more substituents selected from halogen atoms and cyano, alkylsulfonyl, arylsulfonyl, sulfamoyl, sulfonamido, carbamoyl, carbonamido, alkoxy, acyloxy, aryloxy, alkoxycarbonyl, aryloxycarbonyl, ureido, nitro, alkyl, and trifluoromethyl, or Ar is an aryl group substituted with a group which forms a link to a polymeric chain;

$R^1$ is a substituted or unsubstituted phenyl group and $R^2$ is a substituted or unsubstituted alkyl or phenyl group, the $R^1$ and $R^2$ substituents being individually selected from halogen atoms, and alkyl, aryl, alkoxy, aryloxy, carbonamido, carbamoyl, sulfonamido, sulfamoyl, alkylsulfinyl, arylsulfinyl, alkylsulfonyl, arylsulfonyl, alkoxycarbonyl, aryloxycarbonyl, acyl, acyloxy, ureido, imido, carbamate, heterocyclic, cyano, trifluoromethyl, alkylthio, nitro, carboxyl and hydroxyl groups, provided that $R^1$ and $R^2$ each contain at least 6 carbon atoms or the $R^1$ and $R^2$ substituents may individually comprise a group which forms a link to a polymeric chain;

$R^3$ and $R^4$ are individually selected from the group consisting of hydrogen, substituted and unsubstituted alkyl, substituted and unsubstituted phenyl, substituted and unsubstituted alkoxy, substituted and unsubstituted amino, substituted and unsubstituted anilino, substituted and unsubstituted acylamino, halogens and a group which links to a polymer, provided that the total number of carbon atoms contained in $R^3$ and $R^4$ is at least 6 if neither $R^3$ nor $R^4$ is a group which links to a polymer; and X is hydrogen or a coupling-off group selected from the group consisting of halogens, alkoxy, aryloxy, alkylthio, arylthio, acyloxy, sulfonamido, carbonamido, arylazo, nitrogen-containing heterocyclic and imido groups. Coupling-off groups are well known to those skilled in the photographic art. Generally, such groups determine the equivalency of the coupler and modify the reactivity of the coupler. Coupling-off groups can also advantageously effect the layer in which the coupler is coated or other layers in the photographic material by performing, after release from the coupler, such functions as development inhibition, bleach acceleration, color correction, development acceleration and the like. Representative coupling-off groups include, as noted above, halogens (for example, chloro), alkoxy, aryloxy, alkyl thio, aryl thio, acyloxy, sulfonamido, carbonamido, arylazo, nitrogen-containing heterocyclic groups such as pyrazolyl and imidazolyl, and imido groups such as succinimido and hydantoinyl groups. Except for the halogens, these groups may be substituted if desired. Coupling-off groups are described in further detail in: U.S. Pat. Nos. 2,355,169; 3,227,551; 3,432,521; 3,476,563; 3,617,291; 3,880,661; 4,052,212 and 4,134,766, and in British Patent References Nos. 1,466,728; 1,531,927; 1,533,039; 2,006,755A and 2,017,704A, the disclosures of which are incorporated herein by reference.

Preferred structures of magenta couplers are 4- or 2-equivalent pyrazolone couplers, particularly couplers of the structure:

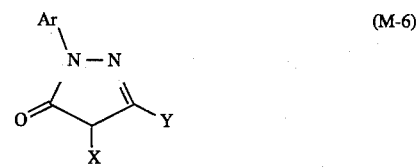

wherein:

Ar is selected from the group consisting of unsubstituted aryl groups, substituted aryl groups and substituted pyridyl groups, the substituents being selected from the group consisting of halogen atoms and cyano, alkylsulfonyl, arylsulfonyl, sulfamoyl, sulfamido, carbamoyl, carbonamido, alkoxy, acyloxy, aryloxy, alkoxycarbonyl, aryloxycarbonyl, ureido, nitro, alkyl and trifluoromethyl groups;

Y is an anilino group substituted with one or more substituents selected from the group consisting of halogen atoms, and alkyl, aryl, alkoxy, aryloxy, carbonamido, carbamoyl, sulfonamido, sulfamoyl, alkylsulfinyl, arylsulfinyl, alkylsulfonyl, arylsulfonyl, alkoxycarbonyl, aryloxycarbonyl, acyl, acyloxy, ureido, imido, carbamate, heterocyclic, cyano, hydroxyl groups, and groups which form a link to a polymeric chain, and wherein Y contains at least 6 carbon atoms; and X is a coupling-off group selected from the group consisting of halogen, alkoxy, aryloxy, alkylthio, arylthio, acyloxy, sulfonamido, sulfonyloxy, carbonamido, arylazo, nitrogen-containing heterocyclic and imido groups.

Coupling-off groups are well known to those skilled in the photographic art. Generally, such groups determine the equivalency of the coupler and modify the reactivity of the coupler. Coupling-off groups can also advantageously effect the layer in which the coupler is coated or other layers in the photographic material by performing, after release from the coupler, such functions as development inhibition, bleach acceleration, color correction, development acceleration and the like. Representative coupling-off groups include, as noted above, halogens (for example, chloro), alkoxy, aryloxy, alkylthio, arylthio, acyloxy, sulfonamido, carbonamido, arylazo, nitrogen-containing heterocyclic groups such as pyrazolyl and imidazolyl, and imido groups such as succinimido and hydantoinyl groups. Coupling-off groups are described in further detail in: U.S. Pat. Nos. 2,355,169; 3,227,551; 3,432,521; 3,476,563; 3,67,291; 3,880,661; 4,052,212 and 4,134,766, and in British Patent Reference Nos. 1,466,788; 1,531,927; 1,533,039; 2,006,755A and 2,017,704A, the disclosures of which are incorporated herein by reference.

Particularly preferred are compounds in which Ar is of the structure:

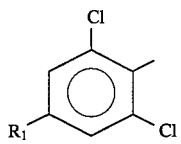

wherein $R_1$ is selected from the group consisting of halogen, cyano, alkylsulfonyl, arylsulfonyl, sulfamoyl, sulfonamido, carbamoyl, carbonamido, ureido, alkoxycarbonyl, aryloxycarbonyl, acyloxy, alkoxy, aryloxy, nitro and trifluoromethyl groups;

Y is of the structure:

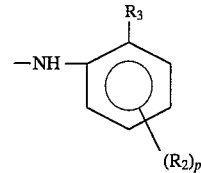

wherein p is from zero to 2 and each $R_2$ is in a meta or para position with respect to $R_3$;

each $R_2$ is individually selected from the group consisting of halogen, alkyl, alkoxy, aryloxy, carbonamido, carbamoyl, sulfonamido, sulfamoyl, alkylsulfinyl, arylsulfinyl, alkylsulfonyl, arylsulfonyl, alkoxycarbonyl, aryloxycarbonyl, acyloxy, ureido, imido, carbamate, heterocyclic, cyano, nitro, acyl, trifluoromethyl, alkylthio and carboxyl groups; and $R_3$ is selected from the group consisting of hydrogen, halogen, alkyl, alkoxy, aryloxy, alkylthio, carbonamido, carbamoyl, sulfonamido, sulfamoyl, alkylsulfonyl, arylsulfonyl, alkoxycarbonyl, acyloxy, acyl, cyano, nitro and trifluoromethyl groups; and X is of the structure:

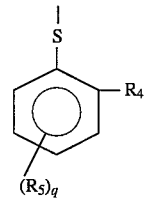

wherein $R_4$ and $R_5$ are individually selected from the group consisting of hydrogen, halogen, alkyl, alkoxy, aryloxy, carbonamido, ureido, carbamate, sulfonamido, carbamoyl, sulfamoyl, acyloxy, alkoxycarbonyl, aryloxycarbonyl, amino and carboxyl groups, and wherein q is 0, 1 or 2 and $R_5$ may be in the meta or para position with respect to the sulfur atom.

Suitable magenta dye-forming couplers for use in the compositions and methods of the present invention include, but are not limited to, the following compounds:

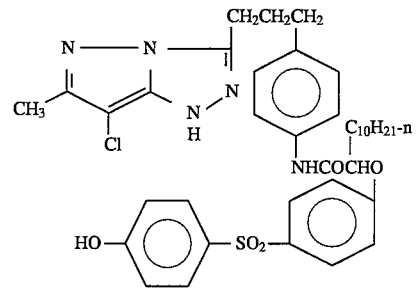

(M-7)

-continued
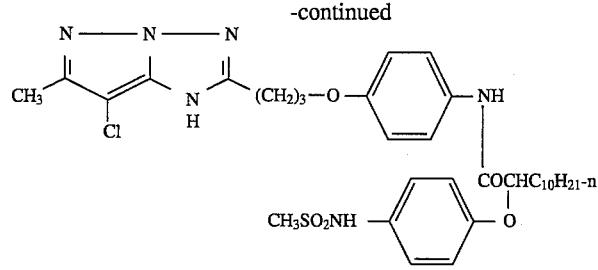
(M-8)
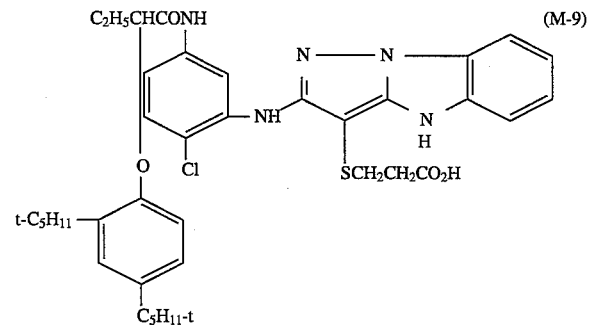
(M-9)
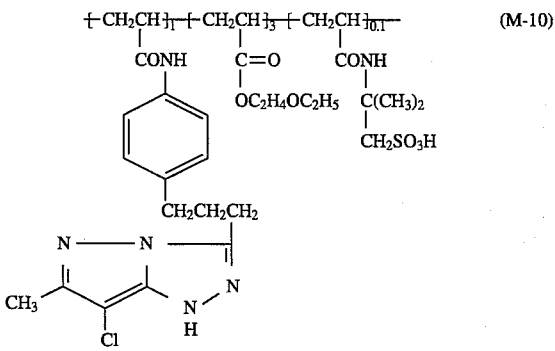
(M-10)
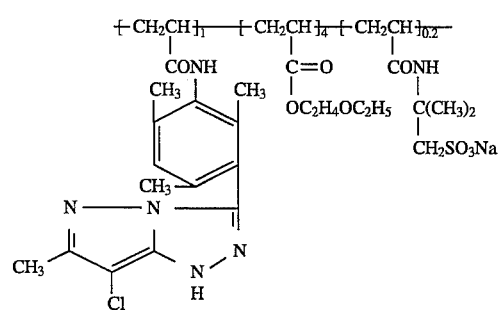
(M-11)
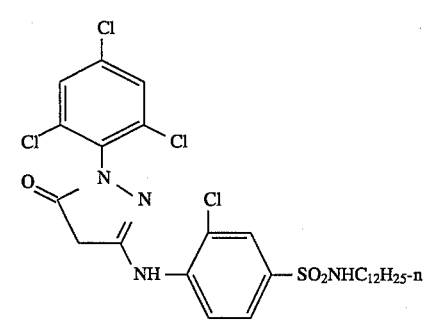
(M-12)
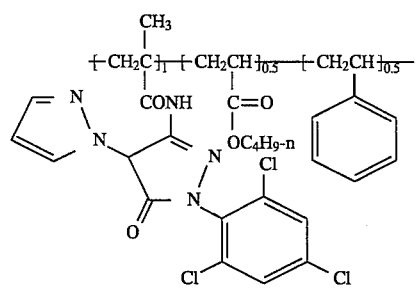
(M-13)
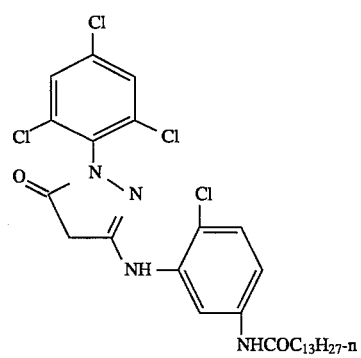
(M-14)
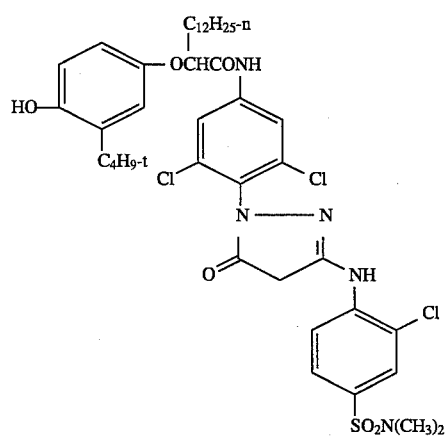
(M-15)
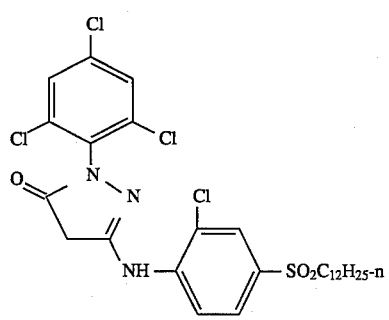
(M-16)

-continued
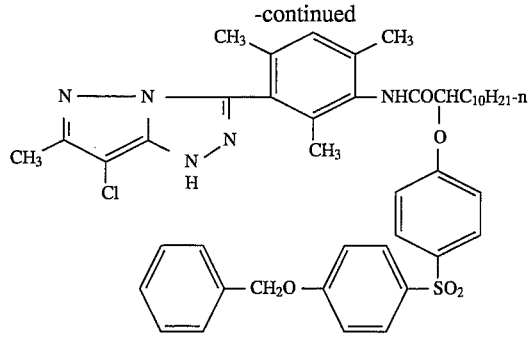
(M-17)
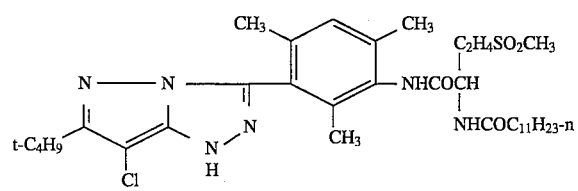
(M-18)
Examples of two-equivalent 3-anilino pyrazolone dye-forming magenta couplers suitable for use in the coupler compositions of the present invention include, but are not limited to the following:
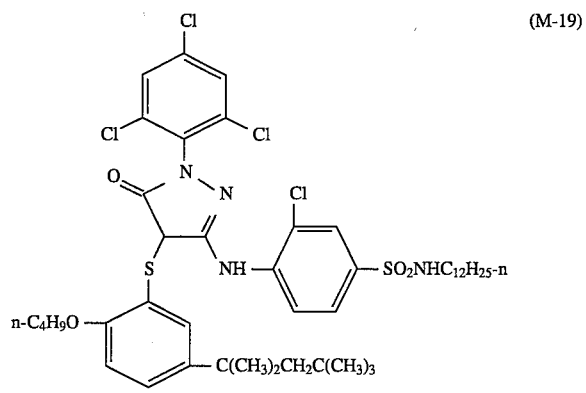
(M-19)
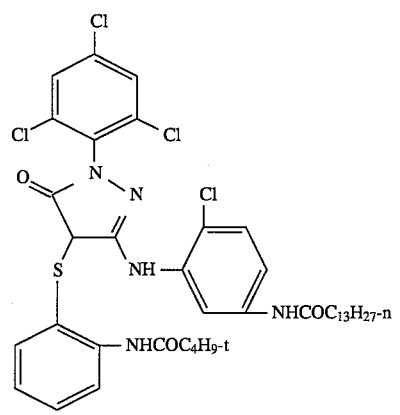
(M-20)
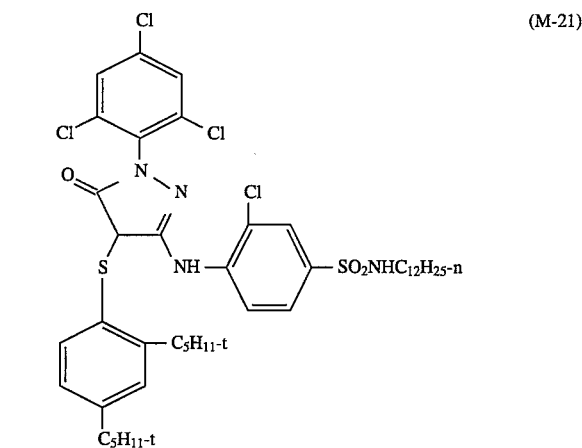
(M-21)
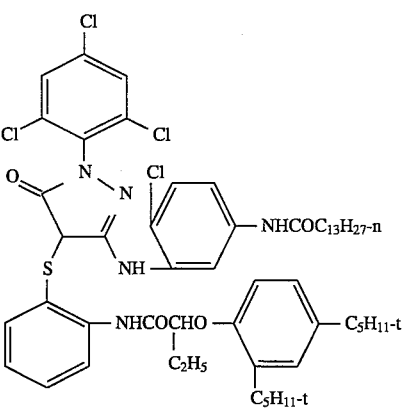
(M-22)

(M-23)
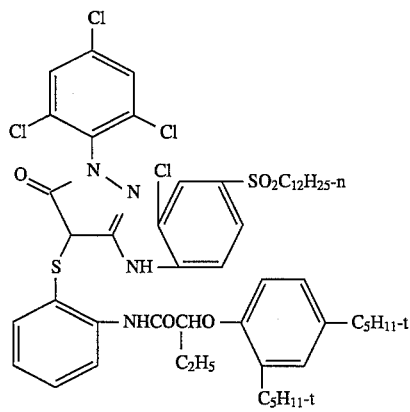
(M-24)
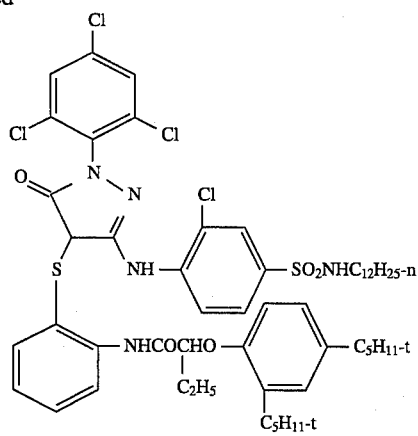
(M-25)
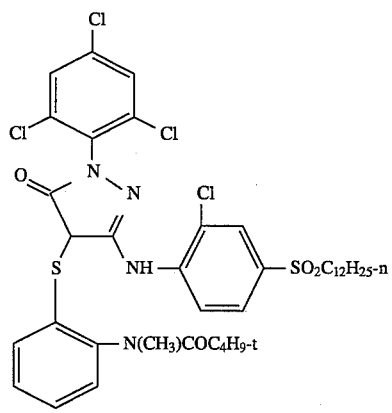
(M-26)
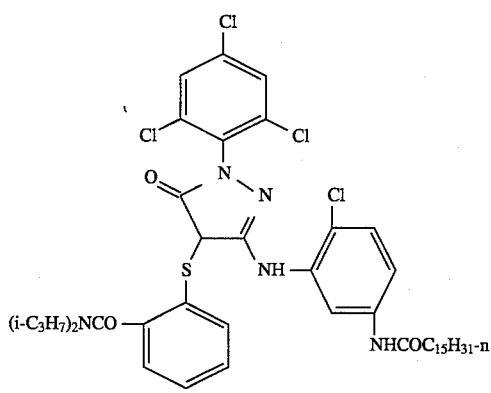
(M-27)
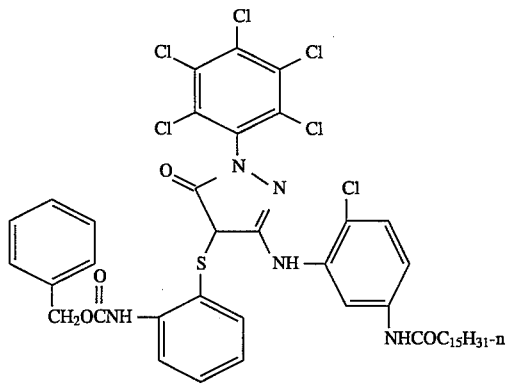
(M-28)
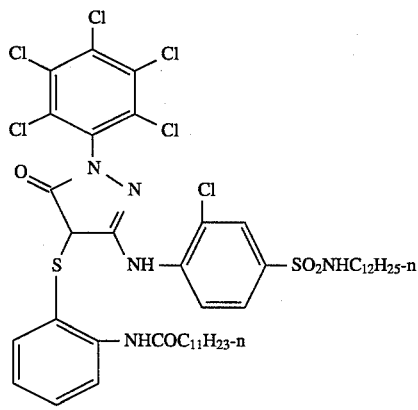
(M-29)
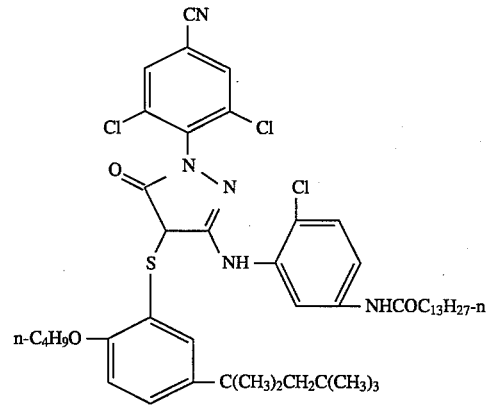

-continued
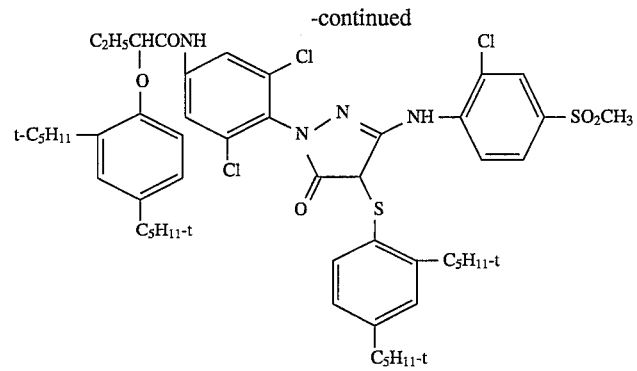
(M-30)
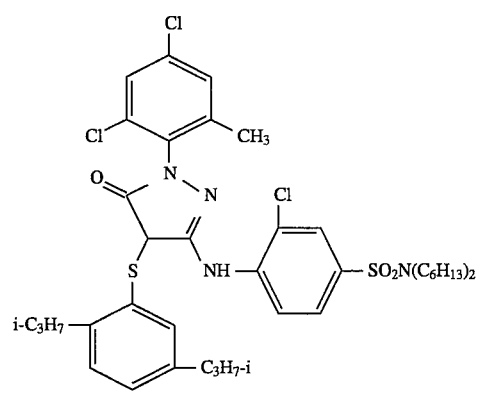
(M-31)
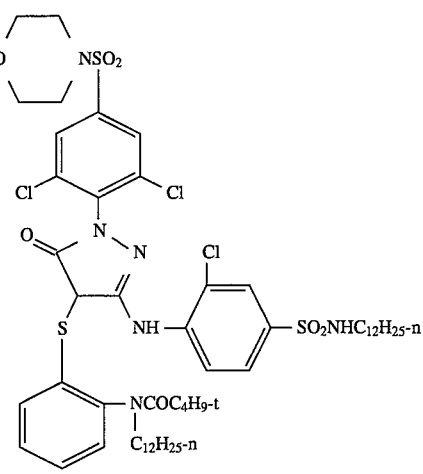
(M-32)
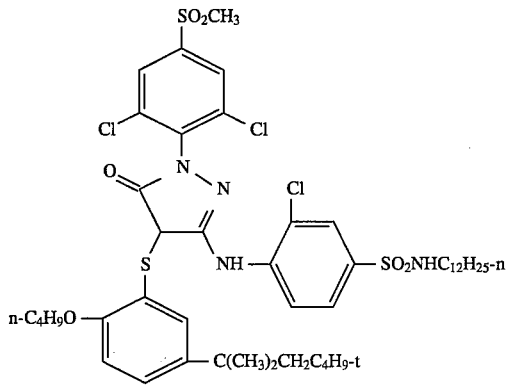
(M-33)
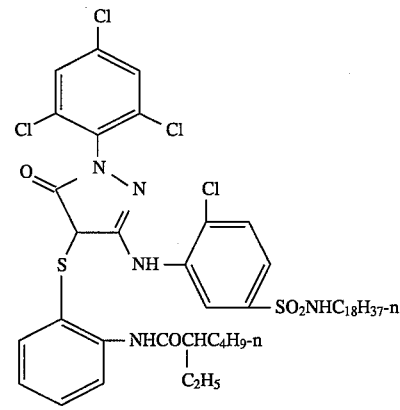
(M-34)
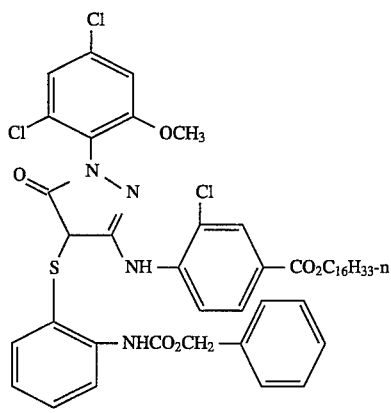
(M-35)
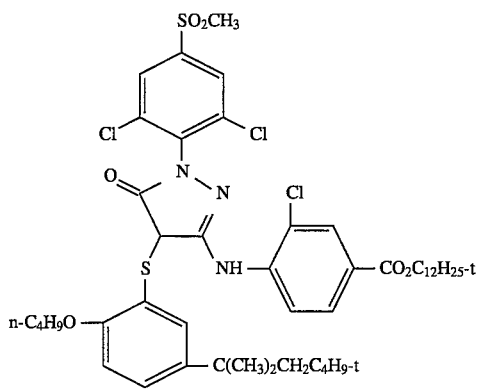
(M-36)

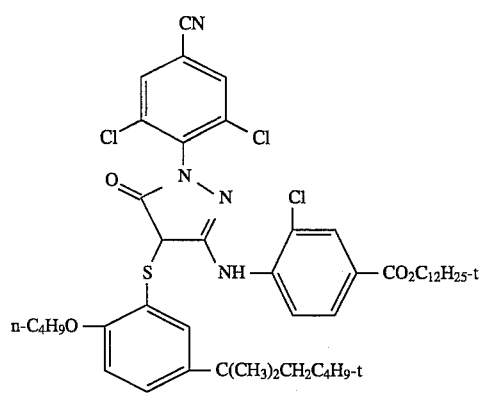
(M-37)

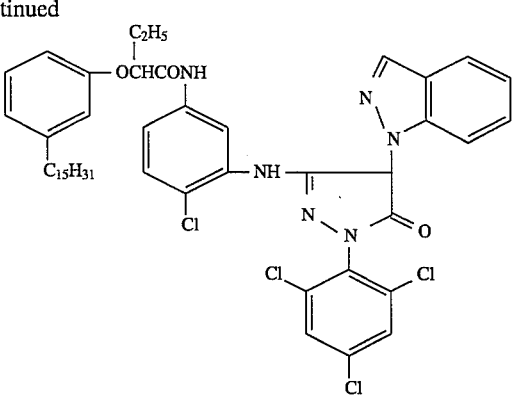
(M-38)

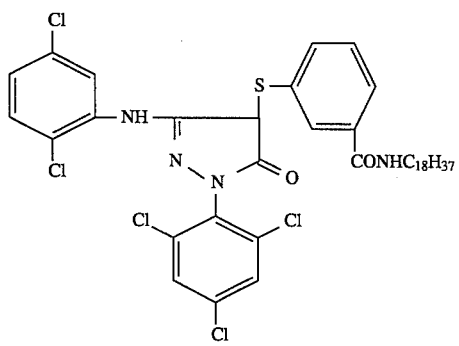
(M-39)

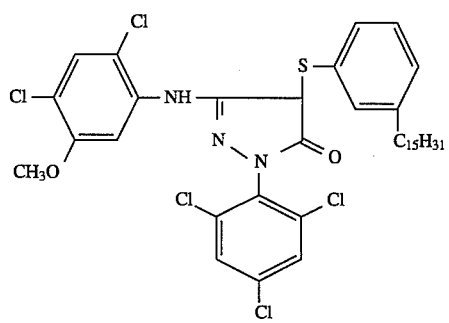
(M-40)

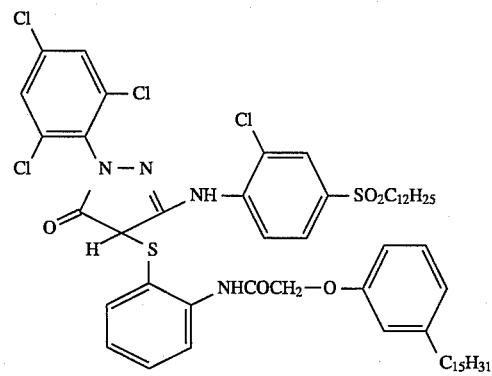
(M-41)

Particularly preferred couplers are the compounds of the formulae M-20, M-21, M-22, M-23, M-24, and M-41.

The color photographic element of this invention comprises, in addition to the magenta coupler-containing layer and the layer comprising the epoxy compound, various other layers typically included in color photographic elements.

Multicolor color photographic elements typically contain image dye-forming units sensitive to each of the three primary regions of the spectrum. Each unit can comprise a single emulsion layer or multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

if desired, the photographic element can be used in conjunction with an applied magnetic layer as described in *Research Disclosure*, November 1992, Item 34390 published by Kenneth Mason Publications, Ltd., Dudley Annex, 12a North Street, Emsworth, Hampshire P010 7DQ, ENGLAND.

In the following discussion of suitable materials for use in the photographic element of this invention, reference will be made to *Research Disclosure*, December 1989, Item 308119, available as described above, which will be identified hereafter by the term "Research Disclosure." The contents of the Research Disclosure, including the patents and publications referenced therein, are incorporated herein by reference, and the Sections hereafter referred to are Sections of the Research Disclosure.

The silver halide emulsions employed in the elements of this invention can be either negative-working or positive-working. Suitable emulsions and their preparation as well as methods of chemical and spectral sensitization are described in Sections I through IV. Color materials and development modifiers are described in Sections V and XXI. Vehicles are described in Section IX, and various additives such as brighteners, antifoggants, stabilizers, light absorbing and scattering materials, hardeners, coating aids, plasticizers, lubricants and matting agents are described, for example, in Sections V, VI, VIII, X, XI, XII, and XVI. Manufacturing methods are described in Sections XIV and XV, other layers and supports in Sections XIII and XVII, processing methods and agents in Sections XIX and XX, and exposure alternatives in Section XVIII.

The photographic element of this invention generally contains image dye-forming couplers that form cyan dyes upon reaction with oxidized color developing agents which are described in such representative patents and publications as: U.S. Pat. Nos. 2,772,162, 2,895,826, 3,002,836, 3,034,892, 2,474,293, 2,423,730, 2,367,531, 3,041,236, 4,883,746 and "Farbkuppler-eine Literature Ubersicht," published in Agfa Mitteilungen, Band III, pp. 156–175 (1961). Preferably such couplers are phenols and naphthols that form cyan dyes on reaction with oxidized color developing agent.

As discussed above, the photographic element of this invention contains an image dye-forming coupler that forms a magenta dye. Illustrative magenta couplers are set forth above.

The photographic element can also contain couplers that form yellow dyes upon reaction with oxidized and color developing agent are described in such representative patents and publications as: U.S. Pat. Nos. 2,875,057, 2,407,210, 3,265,506, 2,298,443, 3,048,194, 3,447,928 and "Farbkuppler-eine LiteraturUbersicht," published in Agfa Mitteilungen, Band III, pp. 112–126 (1961). Such couplers are typically open chain ketomethylene compounds.

It may be useful to use a combination of couplers any of which may contain known ballasts or coupling-off groups such as those described in U.S. Pat. No. 4,301,235; U.S. Pat. No. 4,853,319 and U.S. Pat. No. 4,351,897. The coupler may also be used in association with "wrong" colored couplers (e.g. to adjust levels of interlayer correction) and, in color negative applications, with masking couplers such as those described in EP 213.490; Japanese Published Application 58-172,647; U.S. Pat. No. 2,983,608; German Application DE 2,706,117C; U.K. Patent 1,530,272; Japanese Application A-113935; U.S. Pat. Nos. 4,070,191 and 4,273,861; and German Application DE 2,643,965. The masking couplers may be shifted or blocked.

The photographic element can also contain materials that accelerate or otherwise modify the processing steps e.g. of bleaching or fixing to improve the quality of the image. Bleach accelerator releasing couplers such as those described in EP 193,389; EP 301,477; U.S. Pat. No. 4,163,669; U.S. Pat. No. 4,865,956; and U.S. Pat. No. 4,923,784, may be useful. Also contemplated is use of nucleating agents, development accelerators or their precursors (UK Patent 2,097,140; U.K. Patent 2,131,188); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

For example, in a color paper format, the photographic element of the invention may comprise a support bearing the following layers from top to bottom:

(1) one or more overcoats;

(2) a cyan layer containing "Coupler 1": Butanamide, 2-(2,4-bis(1,1-dimethylpropyl)phenoxy)-N-(3,5-dichloro-2-hydroxy-4-methylphenyl)-, "Coupler 2": Acetamide, 2-(2,4-bis(1,1-dimethylpropyl)phenoxy)-N-(3,5-dichloro-2-hydroxy-4-, and UV Stabilizers: Phenol, 2-(5-chloro-2H-benzotriazol-2-yl)-4,6-bis(1,1-dimetylethyl)-;Phenol, 2-(2H-benzotriazol-2-yl)-4-(1,1-dimethylethyl)-;Phenol, 2-(2H-benzotriazol-2-yl)-4-(1,1-dimethylethyl)-6-(1-methylpropyl)-; and Phenol, 2-(2H-benzotriazol-2-yl)-4,6-bis(1,1-dimethylpropyl)- and a poly(t-butylacrylamide) dye stabilizer;

(3) an interlayer;

(4) a magenta layer containing "Coupler 3": Octanamide, 2-[2,4-bis(1,1-dimethylpropyl)phenoxy]-N-[2-(7-chloro-6-methyl-1H-pyrazolo[1,5-b][1,2,4]triazol-2-yl)propyl]- together with 1,1'-Spirobi(1H-indene), 2,2', 3,3'-tetrahydro-3,3,3', 3'-tetramethyl-5,5', 6,6',-tetrapropoxy-;

(5) an interlayer; and (6) a yellow layer containing "Coupler 4":1-Imidazolidineacetamide, N-(5-((2-(2,4-bis(1,1-dimethylpropyl)phenoxy)-1-oxobutyl)amino)-2-chlorophenyl)-.alpha.-(2,2-dimethyl-1-oxopropyl)-4-ethoxy-2,5-dioxo-3-(phenylmethyl)-. The photographic element of the invention can also contain filter dye layers comprising colloidal silver sol or yellow, cyan, and/or magenta filter dyes, either as oil-in-water dispersions, latex dispersions or as solid particle dispersions. Additionally, the photographic element can contain "smearing" couplers (e.g. as described in U.S. Pat. No. 4,366,237; EP 96,570; U.S. Pat. No. 4,420,556; and U.S. Pat. No. 4,543,323.)

The photographic element can also contain image-modifying compounds such as "Developer Inhibitor-Releasing" compounds (DIR's). DIR's useful in conjunction with the compositions of the invention are known in the art and examples are described in U.S. Pat. Nos. 3,137,57 8; 3,148,022; 3,148,062; 3,227,554; 3,384,657; 3,379,529 ; 3,615,506; 3,617,291; 3,620,746; 3,701,783; 3,733,201 ; 4,049,455; 4,095,984; 4,126,459; 4,149,886; 4,150,228 ; 4,211,562; 4,248,962; 4,259,437; 4,362,878; 4,409,323 ; 4,477,563; 4,782,012; 4,962,018; 4,500,634; 4,579,816 ; 4,607,004; 4,618,571; 4,678,739; 4,746,600; 4,746,601 ; 4,791,049; 4,857,447; 4,865,959; 4,880,342; 4,886,736 ; 4,937, 179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. In a preferred embodiment, the inhibitor moiety or group is selected from the following formulas:

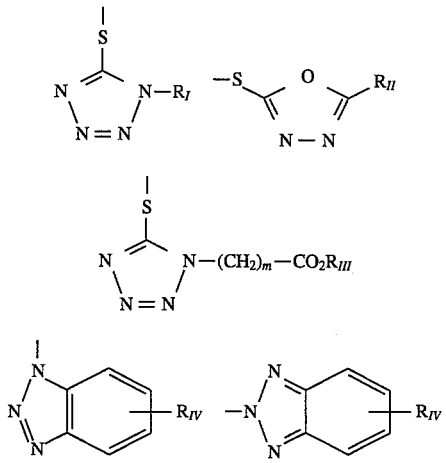

wherein $R_I$ is selected from the group consisting of straight and branched alkyls of from 1 to about 8 carbon atoms, benzyl, phenyl, and alkoxy groups and such groups containing none, one or more than one such substituent; $R_{II}$ is selected from $R_I$ and $—SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, $—COOR_V$ and $NHCOOR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

As mentioned, the developer inhibitor-releasing coupler may include a timing group which produces the time-delayed release of the inhibitor group such as groups utilizing the cleavage reaction of a hemiacetal (U.S. Pat. No. 4,146,396, Japanese Applications 60-249148; 60-249149); groups using an intramolecular nucleophilic substitution reaction (U.S. Pat. No. 4,248,962); groups utilizing an electron transfer reaction along a conjugated system (U.S. Pat. No. 4,409,323; 4,421,845; Japanese Applications 57-188035; 58-98728; 58-209736; 58-209738) groups utilizing ester hydrolysis (German Patent Application (OLS) No. 2,626,315); groups utilizing the cleavage of imino ketals (U.S. Pat. No. 4,546,073); groups that function as a coupler or reducing agent after the coupler reaction (U.S. Pat. No. 4,438,193; U.S. Pat. No. 4,618,571) and groups that combine the features describe above. It is typical that the timing group or moiety is of one of the formulas:

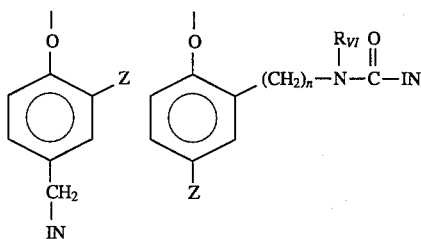

wherein IN is the inhibitor moiety, Z is selected from the group consisting of nitro, cyano, alkylsulfonyl; sulfamoyl ($—SO_2NR_2$); and sulfonamido ($—NRSO_2R$) groups; n is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

Suitable developer inhibitor-releasing couplers for use in the present invention include, but are not limited to, the following:

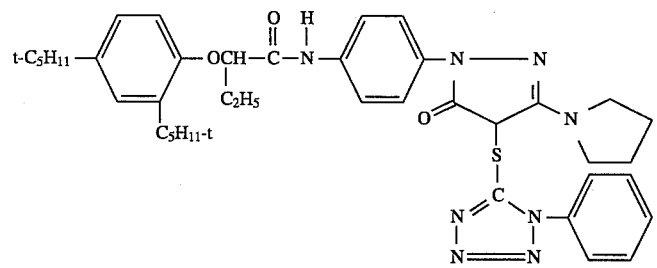

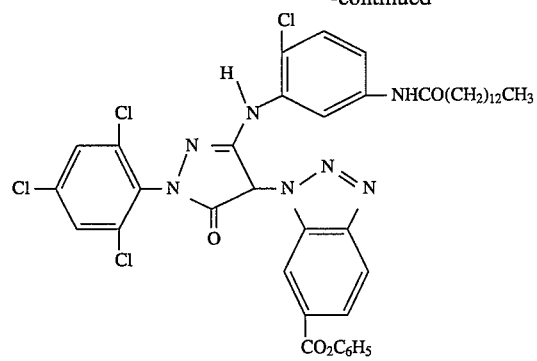
D2
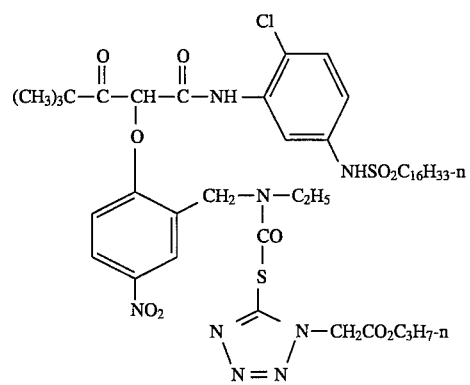
D3
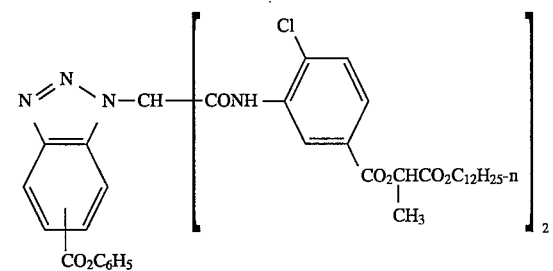
D4
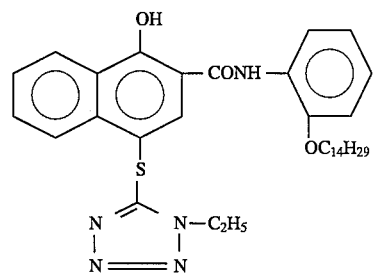
D5

-continued
D6
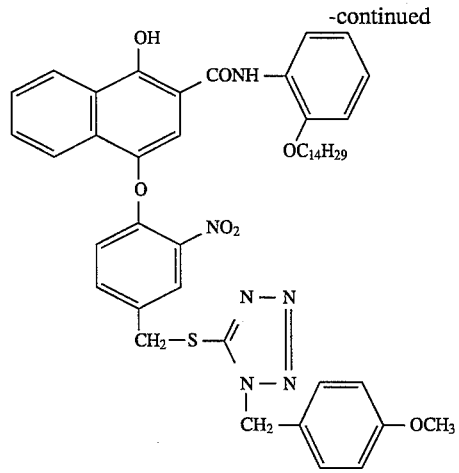
D7
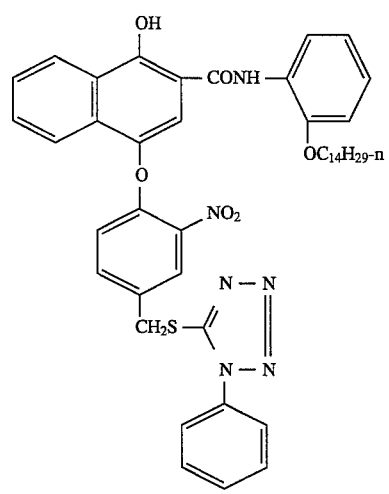
D8
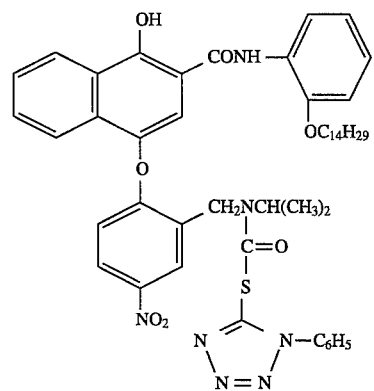

-continued

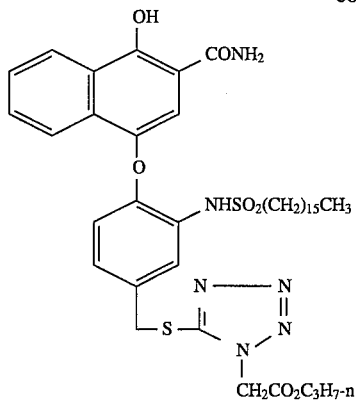

D9

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. Other compounds that can be included in the photographic element of this invention are disclosed in Japanese Published Applications described in Derwent Abstracts having accession numbers as follows: 90-072,629; 90-072,630; 90-072,631; 90-072,632; 90-072,633; 90-072,634; 90-077,822; 90-078,229; 90-078,230; 90-079,336; 90-079,337; 90-079,338; 90-079,690; 90-079,691; 90-080,487; 90-080,488; 90-080,489; 90-080,490; 90-080,491; 90-080,492; 90-080,494; 90-085,928; 90-086,669; 90-086,670; 90-087,360; 90-087,361; 90-087,362; 90-087,363; 90-087,364; 90-088,097; 90-093,662; 90-093,663; 90-093,664; 90-093,665; 90-093,666; 90-093,668; 90-094,055; 90-094,056; 90-103,409; 83-62,586; 83-09,959.

Especially useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $T=ECD/t^2$ where ECD is the average equivalent circular diameter of the tabular grains in microns and t is the average thickness in microns of the tabular grains.

The average useful ECD of photographic emulsions can range up to about 10 microns, although in practice emulsion ECD's seldom exceed about 4 microns. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micron) tabular grains. To achieve the lowest levels of granularity it is preferred that aim tabular grain projected areas be satisfied with ultrathin (t<0.06 micron) tabular grains. Tabular grain thicknesses typically range down to about 0.02 micron. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micron.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions, tabular grains satisfying the stated thickness criteria above account for at least 70 percent of the total grain projected area. In the highest performance tabular grain emulsions, tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616. In addition, use of [100] silver chloride emulsions as described in EP 534,395 are specifically contemplated.

The emulsions can be surface-sensitive emulsions, i.e., emulsions that form latent images primarily on the surfaces of the silver halide grains, or the emulsions can form internal latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

Photographic elements can be exposed to actinic radiation, typically in the visible region of the spectrum, to form a latent image and can then be processed to form a visible dye image. Processing to form a visible dye image includes the step of contacting the element with a color developing agent to reduce developable silver halide and oxidize the color developing agent. Oxidized color developing agent in turn reacts with the coupler to yield a dye.

The photographic elements can be processed, for example, in accordance with color print processes such a the RA-4 process of Eastman Kodak Company as described in the British Journal of Photography Annual of 1988, Pp 198–199.

Preferred color developing agents are phenylenediamines such as: 4-amino-N,N-diethylaniline hydrochloride, 4-amino-3-methyl-N,N-diethylaniline hydrochloride, 4-amino-3-methyl-N-ethyl-N-(b-(methanesulfonamido)

ethyl)aniline sesquisulfate hydrate, 4-amino-3-methyl-N-ethyl-N-(b-hydroxyethyl)aniline sulfate, 4-amino-3-b-(methanesulfonamido)ethyl-N,N-diethylaniline hydrochloride and 4-amino-N-ethyl-N-(2-methoxyethyl)-m-toluidine di-p-toluene sulfonic acid.

Development is usually followed by the conventional steps of bleaching, fixing, or bleach-fixing, to remove silver or silver halide, washing, and drying.

The following examples illustrate the invention.

EXAMPLE 1

(control):

A dispersion of the terminal epoxy compound SI-20 (dispersion A) was prepared in the following manner.

2.0 grams of SI-20 was combined with 2.0 grams of polyvinylpyrrolidone (PVP K-25 from BASF), 0.11 grams of sodium dodecyl sulfate, 29.04 grams of water and 80.57 grams of zirconia beads to constitute the slurry. The slurry was placed on a sweco mill for five days. The zirconia beads were then removed from the slurry by filtration. The aqueous phase was prepared by combining 6.88 grams of a 24% w/w solution of Type IV gelatin with 8.33 grams of distilled water. The pH of the aqueous phase was adjusted to 5.0. 25.0 grams of the ground slurry was then mixed with said aqueous phase to constitute the dispersion.

EXAMPLE 2

(invention):

A second dispersion of the terminal epoxy compound SI-20 (dispersion B) was prepared in the same manner as described above except that 0.5 grams of the high logP liquid tri(2-ethylhexyl) phosphate (logP=9.49) was added to the slurry prior to milling.

A dispersion of the magenta coupler M24 was prepared in the following manner. 14.73 grams of tri(2-ethylhexyl) phosphate was heated as coupler solvent to a temperature of 120° C. and combined with a mixture of 8.53 grams of stabilizer STG-A1 and 2.83 grams of stabilizer ST-3 and 3.4 grams of stabilizer ST-1. This was then combined with 12.75 grams of coupler M24 to constitute the oil phase. The aqueous phase was prepared by mixing 88.5 grams of a 24% w/w solution of Type IV gelatin with 21.2 grams of a 10% w/w solution of the surfactant Alkanol XC and 273 grams of distilled water. The latter was then heated to 70° C. The oil phase was then combined with the aqueous phase and the mixture passed twice through a microfluidizer at a pressure of 10,000 psi at 70° C. to obtain the dispersion.

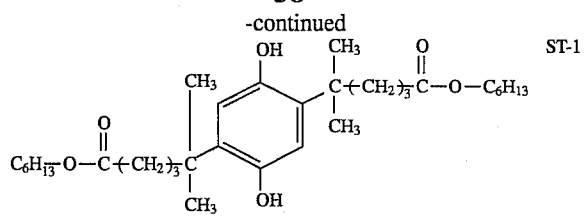

STG-A1

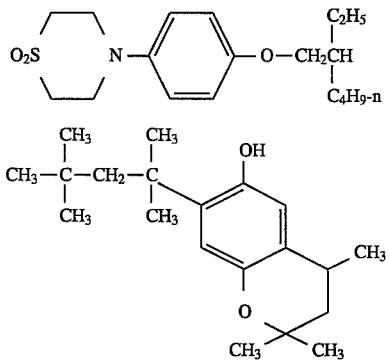

ST-3

-continued

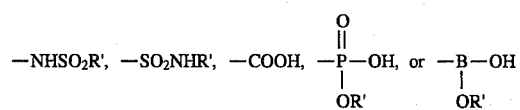

ST-1

The dispersions were then coated on a support in the layer format shown below.

| 215 SI-20 630 Gel |
| 172 Ag 430 M24 1270 Gel |
| 215 SI-20 753 Gel |

All numbers refer to coverages in mg/m². The coatings also contain a UV protection layer and an overcoat(not shown). A set of 35mm strips from these coatings were exposed using a 21 step tablet and processed using the standard RA-4 process. A second set of 35mm strips were treated in the same manner except that these strips were first incubated in an oven at 49° C. and 50% RH for one week prior to exposure and processing. The difference in the green reflection density between the two sets of strips at an exposure corresponding to a density of 1.0 in the first set of strips was noted.

|  | Δ Green 1.0 |
| --- | --- |
| Example 1 (control) | 0.19 |
| Example 2 (invention) | 0.08 |

It is clear that the method of the invention results in coatings that are more stable during raw stock keeping at elevated temperatures.

What is claimed is:

1. A process for preparing a solid particle dispersion of an epoxy compound of the formula SI,

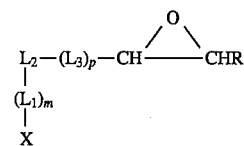

wherein R is H, an alkyl group, or an aryl group; $L_1$ is an alkylene group or arylene group; $L_2$ is —O—, —CO—, —S—, —SO$_2$—, —PO$_2$—, —C$_2$—, —NHCO— or —NHSO$_2$—, wherein $L_2$ may be orientated in either direction; $L_3$ is an alkylene group; m is 0 or 1; p is 0 or 1; and X is $$-NHSO_2R', \quad -SO_2NHR', \quad -COOH, \quad -\underset{\underset{OR'}{|}}{\overset{\overset{O}{\|}}{P}}-OH, \text{ or } -\underset{\underset{OR'}{|}}{B}-OH$$

wherein R' is H or an alkyl or aryl group, with the proviso that where $L_2$ comprises an ionizable group, X may also be an alkyl group or an aryl group;

said process comprising the steps of:
(a) forming a coarse aqueous slurry of solid particles of said compound; and
(b) milling said slurry in the presence of a hydrophobic, photographically inert, liquid second component which has a logP$_{(calc)}$ greater than about 6.0 for time sufficient to provide particles of the desired average particle size.

2. A process according to claim 1, wherein the amount of the second component used in step (b) is less than half the weight of the compound of formula SI.

3. A process according to claim 1, wherein the amount of the second component used in step (b) is less than or about one fourth of the weight of the compound of formula SI.

4. A process according to claim 3, wherein the logP$_{(calc)}$ of said second component is greater than about 8.0.

5. A process according to claim 3, wherein the logP$_{(calc)}$ of said second component is greater than about 9.0.

6. A process according to claim 3, wherein the solubility in water of said second component is less than 1.0 μg/mL.

7. A process according to claim 1, wherein R in Formula SI is H or alkyl.

8. A process according to claim 1, wherein m and p are each 1, $L_1$ is phenylene, $L_2$ is —O—, —CO—, —SO$_2$—, —PO$_2$—, or —CO$_2$—, $L_3$ is a linear or branched alkylene group, X is —NHSO$_2$R', —SONHR', —COOH,

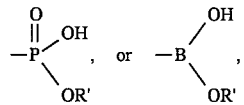

and R' is an alkyl or aryl group.

9. A process according to claim 1, wherein the compound of the formula SI is of the formula:

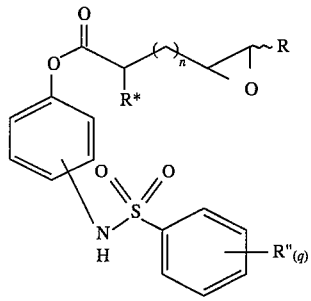

wherein: R* is H or an alkyl or aryl group; n is from 1 to about 20; q is 1, 2, or 3; and each R" is H, an alkoxide group, a phosphate group, a sulfate group, a sulfonamide group, a sulfone group, a halogen atom, or an alkyl group.

10. A process according to claim 1, wherein the logP$_{(calc)}$ of said second component is greater than about 8.0

11. A process according to claim 1, wherein the logP$_{(calc)}$ of said second component is greater then about 9.0.

12. A process according to claim 1, wherein the solubility in water of said second component is less than 1.0 μg/ml.

13. A product produced by the process of claim 1.

14. A product produced by the process of claim 5.

* * * * *

UNITED STATES PATENT AND TRADEMARK OFFICE
CERTIFICATE OF CORRECTION

PATENT NO. : 5,620,632
DATED : April 15, 1997
INVENTOR(S) : Krishnan Chari

It is certified that error appears in the above-identified patent and that said Letters Patent is hereby corrected as shown below:

Column 38, line 47  -- delete "$—C_2—$" and insert therefor -- $—CO_2—$ --

Signed and Sealed this

Thirtieth Day of December, 1997

Attest:

BRUCE LEHMAN

Attesting Officer

Commissioner of Patents and Trademarks